United States Patent [19]

Varma

[11] 4,420,428
[45] Dec. 13, 1983

[54] 16-KETOANDROSTENE-17-DITHIOKETALS

[75] Inventor: Ravi K. Varma, Belle Mead, N.J.

[73] Assignee: E. R. Squibb & Sons, Inc., Princeton, N.J.

[21] Appl. No.: 453,314

[22] Filed: Dec. 27, 1982

[51] Int. Cl.³ ............................................... C07J 7/00
[52] U.S. Cl. ............................................... 260/397.45
[58] Field of Search ................................... 260/397.45

[56] References Cited

U.S. PATENT DOCUMENTS

| | | | |
|---|---|---|---|
| 4,091,036 | 5/1978 | Varma | 260/397.45 |
| 4,094,840 | 6/1978 | Varma | 260/239.55 R |
| 4,133,811 | 1/1979 | Varma | 260/239.55 R |
| 4,146,538 | 3/1979 | Varma et al. | 260/239.55 R |
| 4,361,559 | 11/1982 | Varma | 424/243 |

Primary Examiner—Elbert L. Roberts
Attorney, Agent, or Firm—Lawrence S. Levinson; Donald J. Barrack

[57] ABSTRACT

Steroids having the formual

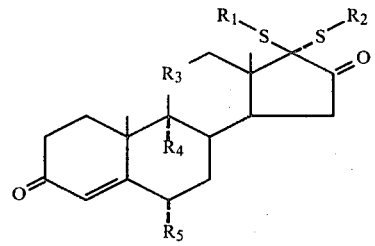

and the 1,2-dehydro and 6,7-dehydro derivatives thereof, wherein $R_1$ and $R_2$ are the same or different and each is alkyl, cycloalkyl or aryl;
$R_3$ is carbonyl, $\beta$-hydroxymethylene or $\beta$-acetyloxymethylene;
$R_4$ is hydrogen or halogen; and
$R_5$ is hydrogen, methyl, hydroxy, alkanoyl, alkanoyloxy, or halogen; have topical anti-inflammatory activity.

13 Claims, No Drawings

16-KETOANDROSTENE-17-DITHIOKETALS

RELATED APPLICATIONS

United States patent application Ser. No. 396,178, filed July 7, 1982, discloses androstene-17-dithioketals having the partial structural formula

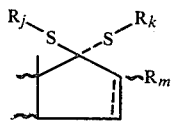

wherein one of $R_j$ and $P_k$ is alkyl, cycloalkyl, aryl, arylalkyl, or —CH$_2$X wherein X is alkylthio, alkoxy, aroyloxy, alkanoyloxy or alkoxycarbonyl and the other is alkylthioalkyl, alkoxyalkyl, alkanoyloxyalkyl, aroyloxyalkyl, alkoxycarbonylalkyl, carboxyalkyl or arylalkyl; $R_m$ is hydrogen, hydroxy, alkoxy, aryloxy, oxo, methylene, alkylthio, arylthio, alkanoyl, alkanoyloxy, or halogen; and the broken line in the 15,16-position represents the optional presence of ethylenic unsaturation. The steroids have antiinflammatory activity.

United States patent application Ser. No. 416,181, filed Sept. 9, 1982, discloses androstene-17-dithioketals having the partial structural formula

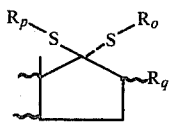

wherein $R_o$ is hydrogen and $R_p$ is alkyl, cycloalkyl, aryl, arylalkyl, alkylthioalkyl, alkoxyalkyl, alkanoyloxyalkyl, aroyloxyalkyl, alkoxycarbonylalkyl, carboxyalkyl, or arylalkyl, or $R_o$ is alkanoyl or aroyl and $R_p$ is alkyl; and $R_q$ is hydrogen, hydroxy, alkoxy, aryloxy, oxo, methylene, alkylthio, arylthio, alkanoyl, alkanoyloxy, or halogen. The steroids are useful intermediates for preparing steroids with antiinflammatory activity.

United States patent application Ser. No. 441,026, filed November 12, 1982, discloses androstene-17-dithioketals having the partial structural formula

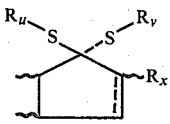

wherein $R_u$ is alkyl, aryl, arylalkyl or cycloalkyl, $R_v$ is alkenyl, substituted alkenyl, alkynyl, substituted alkynyl, mono-, di- or trifluoroalkyl, cyanoalkyl, alkanoylalkyl or

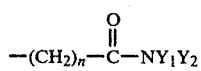

wherein n is 1, 2, 3 or 4 and $Y_1$ and $Y_2$ are the same or different and each is hydrogen or alkyl and $R_x$ is hydrogen, hydroxy, alkoxy, aryloxy, oxo (=O), methylene (=CH$_2$), alkylthio, arylthio, alkanoyl, alkanoyloxy, or fluorine, and the broken line in the 15,16-position represents the optional presence of ethylenic unsaturation. The steroids have antiinflammatory activity.

BACKGROUND OF THE INVENTION

United States Pat. Nos. 4,091,036, issued May 23, 1978, 4,094,840, issued June 13, 1978, 4,133,811, issued Jan. 9, 1979, and 4,146,538, issued Mar. 27, 1979, each discloses androstenes intermediates having the partial structural formula

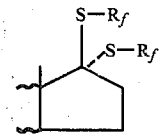

wherein $R_f$ is alkyl or aryl, and both $R_f$ groups are the same.

U.S. Pat. No. 4,361,559, issued Nov. 30, 1982, discloses androstene-17-dithioketals having the partial structural formula

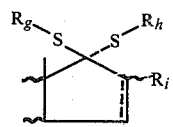

wherein $R_g$ and $R_h$ are the same or different and each is alkyl, cycloalkyl, or aryl; $R_i$ is hydrogen, hydroxy, alkoxy, aryloxy, alkylthio, arylthio,

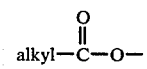

or halogen; and the broken line in the 15,16-position represents the optional presence of ethylenic unsaturation. The steroids have antiinflammatory activity.

BRIEF DESCRIPTION OF THE INVENTION

Steroids having the formula

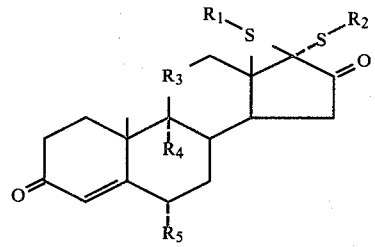

and the 1,2-dehydro and 6,7-dehydro derivatives thereof, have topical antiinflammatory activity. In formula I, and throughout the specification, the symbols are as defined below.

$R_1$ and $R_2$ are the same or different and each is alkyl, cycloalkyl or aryl;

$R_3$ is carbonyl, $\beta$-hydroxymethylene or $\beta$-acetyloxymethylene;

$R_4$ is hydrogen or halogen; and $R_5$ is hydrogen, methyl, hydroxy, alkanoyl, alkanoyloxy, or halogen.

The term "aryl", as used throughout the specification either individually or as part of a larger group, refers to phenyl or phenyl substituted with one or two alkyl, alkoxy or halogen groups.

The term "halogen", as used throughout the specification either individually or as part of a larger group, refers to fluorine, chlorine, bromine and iodine.

The terms "alkyl" and "alkoxy", as used throughout the specification either individually or as part of a larger group, refer to groups having 1 to 12 carbon atoms.

DETAILED DESCRIPTION OF THE INVENTION

The steroids of formula I, and the 1,2-dehydro and 6,7-dehydro derivatives thereof, are topical antiinflammatory agents that can be used to treat skin conditions such as dermatitis, psoriasis, sunburn, eczema, neurodermatitis, or anogential pruritus, and in inhalation therapy for topical treatment of allergy and asthma.

For the treatment of skin conditions, the topical antiinflammatory steroids of this invention may be administered in a conventional pharmaceutical carrier in the form of a cream, ointment, lotion or the like. The steroids will preferably be used in the range of 0.01 to 5.0% by weight of the vehicle, preferably 0.05 to 2.0% by weight of the vehicle.

For the topical treatment of allergy and asthma the topical antiinflammatory steroids of this invention may be administered in the conventional manner, e.g., as solid medicament which has been atomized. U.S. Pat. Nos. 3,948,264 and 4,147,166 are exemplary of the literature which describes devices that can be used to administer solid medicaments for inhalation therapy.

The steroids of formula I, and the 1,2-dehydro and 6,7-dehydro derivatives therof, wherein $R_1$ and $R_2$ are the same, can be prepared by oxidizing the corresponding 16α-hydroxyandrostene having the formula

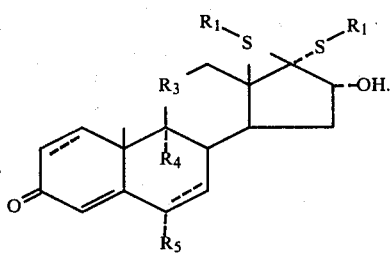

The oxidation is preferably accomplished using a mixture of dimethylsulfoxide and acetic anhydride.

The steroid of formula I, and the 1,2-dehydro and 6,7-dehydro derivatives thereof, wherein $R_1$ and $R_2$ are different, can be prepared by first heating a 16α-methoxy-17-symmetrical dithioketal androstene having the formula

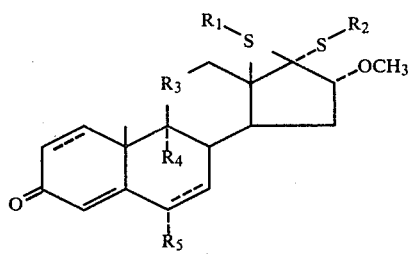

to yield the corresponding (unstable) androstene having the formula

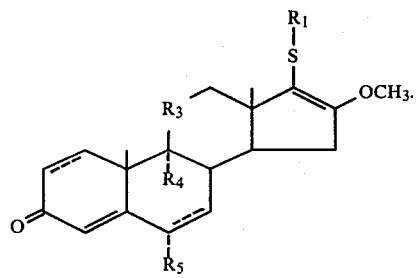

The androstene of formula IV is hydrolyzed directly (i.e., the steroid of formula IV is not isolated) with dilute mineral acid to yield the corresponding androstene having the formula

V

Conversion of an androstene of formula V to the desired product of formula I can be accomplished by reaction with the appropriate compound having the formula $$R_2-S-SO_2-R_2. \qquad VI$$

The reaction will preferably be run in an organic solvent such as tetrahydrofuran in the presence of a base such as n-butyl lithium and a secondary amine such as diisopropylamine.

Alternatively, the steroids of formula I, and the 1,2-dehydro and 6,7-dehydro derivatives thereof, wherein $R_1$ and $R_2$ are different, can be prepared by first oxidizing an androstene of formula II with a peracid (e.g., m-chloroperbenzoic acid), preferably in an organic solvent, to yield the corresponding androstene having the formula

VII

Reaction of an androstene of formula VII with dimethylsulfoxide and acetic anhydride yields the corresponding androstene of formula V. Conversion of an androstene of formula V to a product of formula I can be accomplished using the procedure described above.

In the above-described reactions it may be necessary (when, in the desired product, $R_3$ is β-hydroxymethylene) to protect the 11β-hydroxyl group of the steroid starting materials and intermediates. An exemplary family of protecting groups is the acyl family, e.g., alkanoyl groups such as acetyl. Means for protection and deprotection of the 11β-hydroxyl group are well known in the art.

The preparation of steroids of formulas II and III is disclosed in United States patent application Ser. No. 294,680, filed Aug. 20, 1981; that disclosure is incorporated herein by reference.

The compounds of formula VI can be prepared using art-recognized techniques; see, for example, D. J. Smith et al., *Biochemistry*, 14, 766 (1975).

The following examples are specific embodiments of this invention.

EXAMPLE 1

9-Fluoro-11β-hydroxy-17,17-bis(methylthio)androsta-1,4-diene-3,16-dione (A) 11β-(Acetyloxy)-9-fluoro-17-(methylsulfonyl)androsta-1,4,16-trien-3-one To a solution of 20 g (51.34 mmole) of 11β-(acetyloxy)-17-(methylthio)-9-(fluoro)androsta-1,4,16-trien-3-one in dichloromethane (350 m) was added 22.8 g (113 mmole) of m-chloroperoxybenzoic acid (85.6%) in 350 ml of dry dichloromethane and the solution was stirred at room temperature under nitrogen for 40 minutes. It was then washed with a saturated sodium bicarbonate solution and water, dried over anhydrous $Na_2SO_4$ and evaporated in vacuo to give 21.4 g of the title compound, melting point 273°–275° C., dec.

(B) 11β-(Acetyloxy)-9-fluoro-16α-hydroxyandrosta-1,4-diene-3,17-dione

A solution of 21 g of 11β-(acetyloxy)-9-fluoro-17-(methylsulfonyl)androsta-1,4,16-trien-3-one and 65 ml of formic acid (10%, $V/V$) in 1.7 liters of acetone (reagent grade) was cooled to −10° C. (salt-ice bath). A solution of 19 g of potassium permanganate in 650 ml of acetone (reagent grade) was added at −10° C. over the course of 20 minutes. The mixture was stirred at approximately −10° C. for 45 minutes, quenched with a solution of 5% sodium bisulfite (300 ml) and acetone (300 ml), and gradually warmed up to room temperature. Hyflo was added and the mixture was filtered through a bed of Hyflo. The filtrate was evaporated in vacuo to give a slurry. This was extracted with chloroform, and the chloroform solution was washed with water, dried over anhydrous $Na_2SO_4$ and evaporated in vacuo to give a foam. This was dissolved in chloroform-hexane (7:3) and chromatographed on a 100 g-silica gel column, eluting successively with chloroform-hexane (7:3 and 9:1), chloroform, chloroform-ethyl acetate (4:1) and chloroform-methanol (9:1) to give 9.5 g of the title compound, melting point 241°–243° C., and 4.0 g of its 16β-hydroxy isomer, melting point 229°–231° C., dec.

(C) 11β-(acetyloxy)-9-fluoro-16α-hydroxy-17,17-bis(methylthio)androsta-1,4-dien-3-one A solution of 9.5 g (25.2 mmole) of 11β-(acetyloxy)-9-fluoro-16α-hydroxyandrosta-1,4-diene-3,17-dione in glacial acetic acid (100 ml) and dry dichloromethane (50 ml) was cooled in an ice bath. A solution of methyl mercaptan in dry dichloromethane (2 M, 100 ml), and then boron trifluoride etherate (8 ml) were added. The solution was stirred at 0° C. under nitrogen for 45 minutes, poured into cold water and extracted with chloroform. The chloroform solution was washed with a saturated sodium bicarbonate solution and water, dried over anhydrous $Na_2SO_4$ and evaporated in vacuo to give a foam (13 g). This was mixed with acetone (400 ml), water (25 ml) and iodomethane (13 ml) and refluxed for 75 minutes. The solvent was evaporated in vacuo at 30°–35° C. to give a slurry; heating above 30°–35° C. was avoided. The slurry was diluted with chloroform, washed with a 10% sodium thiosulfate solution and water, dried over anhydrous $Na_2SO_4$ and evaporated in vacuo to give a foam. This was dissolved in chloroform-hexane (3:2) and chromatographed on a 100 g-silica gel column, eluting successively with chloroform-hexane (3:2 and 7:3), chloroform and chloroform-ethyl acetate (9:1) to give 6.3 g of a slightly impure title compound. Crystallization from ethyl acetate-hexane gave 6.0 g of material, melting point 218°–200° C.

(D) 11β-(Acetyloxy)-9-fluoro-17,17-bis(methylthio)androsta-1,4-diene-3,16-dione

A solution of 3.0 g (6.6 mmole) of 11β-(acetyloxy)-9-fluoro-16α-hydroxy-17,17-bis(methylthio)androsta-1,4-dien-3-one in a solution of dry dimethylsulfoxide (30 ml), acetic anhydride (20 ml) and glacial acetic acid (10 ml) was stirred at room temperature under nitrogen overnight. The resulting solution was poured into cold water and extracted with dichloromethane. The dichloromethane solution was washed with saturated sodium bicarbonate solution and water, dried over anhydrous $Na_2SO_4$ and evaporated in vacuo to give 2.9 g of solid, melting point 225°–227° C.

(E) 9-Fluoro-11β-hydroxy-17,17-bis(methylthio)androsta-1,4-diene-3,16-dione

To a stirred solution of 1.7 g (3.76 mmole) of 11β-(acetyloxy)-9-fluoro-17,17-bis(methylthio)androsta-1,4-diene-3,16-dione in a mixture of methanol (70 ml), tetrahydrofuran (50 ml) and water (5 ml) was added 10% potassium carbonate solution dropwise until the pH of solution was about 10. The solution was allowed to stir at room temperature under nitrogen for 2 hours and quenched with a slight excess of concentrated acetic acid. The solvent was evaporated in vacuo to give a slurry. This was diluted with water and extracted with dichloromethane. The dichloromethane solution was dried over anhydrous $Na_2SO_4$ and evaporated in vacuo to give 1.35 g of the title compound. Recrystallization of this from acetone-hexane gave 720 mg of an analytical specimen, melting point 293°–294° C., dec.

Anal. Calc'd for $C_{21}H_{27}FO_3S_2$: C, 61.43; H, 6.63; F, 4.63; S, 15.62. Found: C, 61.42; H, 6.43; F, 4.60; S, 15.79.

EXAMPLE 2

17α-(Ethylthio)-9-fluoro-11β-hydroxy-17-(methylthio)androsta-1,4-diene-3,16-dione (A) 11β-(Acetyloxy)-9-fluoro-16α-hydroxy-17α-methylsulfinyl-17-(methylthio)androsta-1,4-diene-3-one To a cold solution of 2.5 g (5.62 mmole) of 11β-(acetyloxy)-9-fluoro-16α-hydroxy-17,17-bis-(methylthio)androsta-1,4-dien-3-one (see example 1C) in a mixture of dichloromethane (100 ml) and methanol (20 ml) at −78° C. (acetone-Dry ice bath) was added a solution of 1.4 g (5.62 mmole) of m-chloroperoxybenzoic acid (85%) in dichloromethane (20 ml) over the course of 3 minutes. The resulting solution was gradually warmed to 0° C. over the course of 1.5 hours, poured into cold water and extracted with dichloromethane. The dichloromethane solution was washed with saturated NaHCO$_3$ solution and water, dried over anhydrous $Na_2SO_4$ and evaporated in vacuo at 30° C. to give 2.54 g of the title compound. (This compound is not very stable on standing and must be used as soon as it is prepared).

(B) 11β-(Acetyloxy)-9-fluoro-17-(methylthio)androsta-1,4-diene-3,16-dione

A solution of 11β-(acetyloxy)-9-fluoro-16α-hydroxy-17α-(methylsulfinyl)-17-(methylthio)androsta-1,4-diene-3-one (50 mg) in a mixture of dry dimethylsulfoxide (3.0 ml), acetic anhydride (2 ml) and acetic acid (1 ml) was stirred at room temperature for 4.0 hours. The mixture was then poured into cold water and extracted with dichloromethane. The extracts were combined, washed with water, dried (anhydrous MgSO$_4$), and evaporated. The residue was crystallized from ethyl acetate-hexane to afford the title compound (36 mg), melting point 235°–237° C.

(C) Ethyl ethanethiosulfonate

Ethyl disulfide (36.68 g, 0.3 mole) was dissolved in 90 ml of glacial acetic acid in a 500 ml three neck flask fitted with a reflux condenser and a 100 ml-dropping funnel. The reaction flask was first cooled to 0° C. with vigorous stirring. A solution of 68.1 g of hydrogen peroxide (30%) was added slowly through the dropping funnel while maintaining the temperature below 10° C. Initially the reaction mixture existed as two layers. After addition of hydrogen peroxide, the solution was stirred for 30 minutes at 0° C. and the flask was then slowly warmed to 60° C. for about 1.0 hours. The reaction mixture gradually became a homogeneous solution. (Warming the flask slowly is essential to prevent the reaction from becoming extremely exothermic.) After tests for peroxide became negative (KI-starch paper), the glacial acetic acid was removed in vacuo at 40° C. The oil was diluted with 150 ml of saturated NaHCO$_3$ and extracted thoroughly with chloroform. The chloroform solution was dried over anhydrous Na$_2$SO$_4$ and evaporated in vacuo to give an oil. Distillation under 1.5 mm of Hg gave 37.5 g of the title compound, boiling point 90°–96° C.

(D) 11β-(Acetyloxy)-17α-(ethylthio)-9-fluoro-17-(methylthio)androsta-1,4-diene

To a solution of 76 mg (0.75 mmole) of diisopropylamine in 2 ml of dry tetrahydrofuran at −78° C. (acetone-Dry ice bath) was added dropwise 0.44 ml of n-butyl lithium (1.7 M in hexane) under nitrogen. After stirring 40 minutes at −78° C., a solution of 203 mg (0.5 mmole) of 11β-(acetyloxy)-9-fluoro-17β-(methylthio)androsta-1,4-diene-3,16-dione in 2 ml of dry tetrahydrofuran was added dropwise. The mixture was gradually warmed to 0° C. over the course of 1.0 hour. This was slowly added to a solution of 771 mg (5 mmole) of ethyl ethanethiosulfonate in 2 ml of dry tetrahydrofuran at 0° under nitrogen. After stirring for 30 minutes, the resulting solution was poured into water and extracted with chloroform. The chloroform solution was dried over anhydrous Na$_2$SO$_4$ and evaporated in vacuo to give an oil. This was dissolved in chloroform and chromatographed on 2 precoated silica gel TLC plates (E. Merck, 20 cm×20 cm×0.5 mm, 1:4 ethyl acetate-chloroform for development) to give 46 mg of the title compound.

A second run using 406.5 mg (1 mmole) of 11β-(acetyloxy)-9-fluoro-17β-(methylthio)androsta-1,4-diene-3,16-dione gave an additional 114 mg of the title compound.

(E) 17α-(Ethylthio)-9-fluoro-11β-hydroxy-17-(methylthio)androsta-1,4-diene-3,16-dione A solution of 160 mg (0.343 mmole) of 11β-(acetyloxy)-17α-(ethylthio)-9-fluoro-17-(methylthio)androsta-1,4-diene-3,16-dione in a mixture of methanol (10 ml) tetrahydrofuran (5 ml) and water (0.1 ml) was stirred with 0.7 ml of a 3 N sodium hydroxide solution at room temperature under nitrogen for 1.0 hour. The resulting solution was quenched with a slight excess of concentrated acetic acid. The solvent was evaporated in vacuo to give a slurry, which was diluted with water and extracted with chloroform. The chloroform solution was dried over anhydrous Na$_2$SO$_4$ and evaporated in vacuo to give a foam (135 mg). This was dissolved in chloroform-hexane (7:3) and chromatographed on a 15 g-silica gel column, eluting with chloroform-hexane (7:3) to give 115 mg of the title compound. Crystallization from acetone-hexane gave 90 mg of analytical specimen, melting point 262°–264° C., dec.

EXAMPLE 3

17,17-bis(Ethylthio)-9-fluoro-11β-hydroxyandrosta-1,4-diene-3,16-dione (A) 11β-(Acetyloxy)-17,17-bis(ethylthio)-9-fluoro-16α-hydroxyandrosta-1,4-diene-3-one To a solution of 11β-(acetyloxy)-9-fluoro-16α-hydroxyandrosta-1,4-dien-3,17-dione (1.0 g; see example 1B) in glacial acetic acid (30 ml) containing ethanethiol (1.0 ml), undistilled boron trifluoride etherate (1.2 ml) was added. After 1.0 hour, an additional 1.0 ml each of ethanethiol and boron trifluoride etherate were added, and three minutes later, the solution was added to water and extracted with chloroform. The chloroform solution was washed with water, a dilute NaHCO$_3$ solution and water, dried (MgSO$_4$) and evaporated to afford the crude product as a gum. This was subjected to preparative thin layer chromatography on four Analtech 2×200×200 mm silica gel plates using chloroform-ethyl acetate (9:1) for developments and chloroform-methanol (4:1) for extraction of the bands to isolate, in the order of increasing polarity, 11β,16α-di(acetyloxy)-17,17-bis(ethylthio)-9-fluoroandrosta-1,4-diene-3,17-dione (147 mg), the title compound (314 mg; after one crystallization from ethyl acetate-hexane, melting point was 181°–182° C.), an uncharacterized compound (40 mg) and the starting steroid (430 mg).

(B) 11β-(Acetyloxy)-17,17-bis(ethylthio)-9-fluoroandrosta-1,4-diene-3,16-dione

A solution of 11β-(acetyloxy)-17,17-bis-(ethylthio)-9-fluoro-16α-hydroxyandrosta-1,4-dien-3-one (100 mg, 0.207 mmole) in a mixture of dry dimethylsulfoxide (2.0 ml), acetic anhydride (0.7 ml) and acetic acid (0.1 ml) was left standing at room temperature for 18 hours. The mixture was then added to water and was extracted with chloroform. The chloroform solution was washed with water, dried (MgSO$_4$) and evaporated to afford the title compound (94 mg) as a solid.

(C) 17,17-bis(Ethylthio)-9-fluoro-11β-hydroxyandrosta-1,4-diene-3,16-dione

11β-(Acetyloxy)-17,17-bis(ethylthio)-9-fluoroandrosta-1,4-diene-3,16-dione was dissolved in a mixture of methanol (3.0 ml) and tetrahydrofuran (3.0 ml) and was exposed to 3 M sodium hydroxide (0.3 ml) for 1.0 hour under an atmosphere of nitrogen. The mixture was then added to water and was extracted with chloroform. The chloroform solution was washed with water, dried (MgSO$_4$) and was evaporated to afford the title compound as a solid (80 mg). One crystallization of this form ethyl acetate-hexane followed by drying gave the analytical specimen of the title compound (58 mg), melting point 268°–270° C. (dec., discoloration starts from ca. 200° C.).

EXAMPLE 4

9-Fluoro-11β-hydroxy-17β-(methylthio)-17-(propylthio)androsta-1,4-diene-3,16-dione (A) n-Propyl n-propanethiosulfonate n-Propyl disulfide (37.575 g, 0.25 mole) was dissolved in 90 ml of glacial acetic acid in a 500 ml three-neck flask fitted with a reflux condenser and 100 ml dropping funnel. The reaction flask was first cooled to 0° C., and with vigorous stirring, a solution of 56.7 g (0.5 mole) of hydrogen peroxide (30%) was added slowly through the dropping funnel while maintaining the temperature below 10° C. Initially the reaction mixture existed as two layers. After addition of hydrogen peroxide, the solution was stirred for 30 minutes at 0° C. and the flask was then slowly warmed to 60° C. over the course of one hour, while it gradually became a homogeneous solution. [Slow warming of the flask was necessary; otherwise the reaction becomes extremely exothermic.] After a test for peroxide became negative (KI-starch paper), the glacial acetic acid was removed in vacuo at 45° C. The oil was diluted with 150 ml of saturated NaHCO₃ solution and extracted throughly with chloroform. The chloroform solution was dried over anhydrous Na₂SO₄ and evaporated in vacuo to give an oil. Distillation under 2.0 mm of Hg gave 29.1 g of the title compound, boiling point 110°–115° C.

(B) 11β-(Acetyloxy)-9-fluoro-17β-(methylthio)-17-(propylthio)androsta-1,4-diene-3,16-dione To a solution of 76 mg (0.75 mmole) of diisopropylamine in 2 ml of dry tetrahydrofuran at −78° C. (acetone-Dry ice bath) was added dropwise 0.44 ml of n-butyllithium (1.7 M in hexane) under nitrogen. After stirring 10 minutes at −78° C., a solution of 203 mg (0.5 mmole) of 11β-(acetyloxy)-9-fluoro-17β-(methylthio)androsta-1,4-diene-3,16-dione (see example 2B) in 2.5 ml of dry tetrahydrofuran was added dropwise. The mixture was gradually warmed to 0° C. over the course of 1.5 hours. This was slowly added to a solution of 791.5 mg (5 mmole) of n-propyl n-propanethiosulfonate in 2 ml of dry tetrahydrofuran at 0° C. under nitrogen. After stirring for 45 minutes, the resulting solution was poured into water and extracted with chloroform. The chloroform solution was dried over anhydrous Na₂SO₄ and evaporated in vacuo to give an oil. This was dissolved in 1:1 chloroform-hexane and chromatographed on a 20 g-silica gel column, eluting successively with chloroform-hexane (1:1) and chloroform to give 72 mg of the title compound.

Another run on the same scale gave 80 mg more of the title compound.

(C) 9-Fluoro-11β-hydroxy-17β-(methylthio)-17-(propylthio)androsta-1,4-diene-3,16-dione A solution of 152 mg (0.316 mmole) of 11β-(acetyloxy)-9-fluoro-17β-(methylthio)-17-(propylthio)androsta-1,4-diene-3-,16-dione on a mixture of methanol (15 ml), tetrahydrofuran (10 ml) and water (1 ml) was stirred with 1.0 ml of 3 M sodium hydroxide solution at room temperature under nitrogen for one hour. The resulting solution was quenched with a slight excess of acetic acid. The solvent was evaporated in vacuo to give a slurry. This was diluted with water and extracted with chloroform. The chloroform solution was dried over anhydrous Na₂SO₄ and evaporated in vacuo to give a foam. This was redissolved in a small amount of chloroform and chromatographed on 3 precoated silica gel TLC plates (E. Merck, 20 cm×20 cm×0.5 mm, 1:4 ethyl acetate-chloroform for development) to give the title compound. Crystallization from acetone-hexane gave 115 mg of an analytical specimen, melting point 246°–248° C. (dec.).

What is claimed is:

1. A steroid having the formula

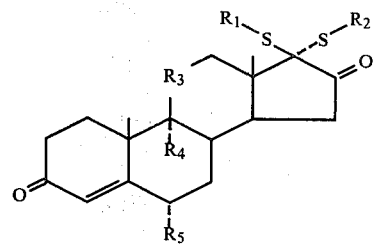

or 1,2-dehydro and 6,7-dehydro derivatives thereof, wherein $R_1$ and $R_2$ are the same or different and each is alkyl, cycloalkyl or aryl;

$R_3$ is carbonyl, β-hydroxymethylene or β-acetyloxymethylene;

$R_4$ is hydrogen or halogen; and $R_5$ is hydrogen, methyl, hydroxy, alkanoyl, alkanoyloxy, or halogen.

2. A steroid in accordance with claim 1 wherein $R_3$ is β-hydroxymethylene.

3. A steroid in accordance with claim 1 wherein $R_4$ is fluorine.

4. A steroid in accordance with claim 1 wherein $R_5$ is hydrogen.

5. A steroid in accordance with claim 1 wherein $R_3$ is β-hydroxymethylene, $R_4$ is fluorine and $R_5$ is hydrogen.

6. A steroid in accordance with claim 1 wherein $R_1$ and $R_2$ are each methyl.

7. A steroid in accordance with claim 5 wherein $R_1$ and $R_2$ are each methyl.

8. A steroid in accordance with claim 1 wherein one of $R_1$ and $R_2$ is methyl and the other is ethyl.

9. A steroid in accordance with claim 5 wherein one of $R_1$ and $R_2$ is methyl and the other is ethyl.

10. The steroid in accordance with claim 1, 9-fluoro-11β-hydroxy-17,17-bis(methylthio)androsta-1,4-diene-3,16-dione.

11. The steroid in accordance with claim 1, 17α-(ethylthio)-9-fluoro-11β-hydroxy-17-(methylthio)androsta-1,4-diene-3,16-dione.

12. The steroid in accordance with claim 1, 17,17-bis(ethylthio)-9-fluoro-11β-hydroxyandrosta-1,4-diene-3,16-dione.

13. The steroid in accordance with claim 1, 9-fluoro-11β-hydroxy-17β-(methylthio)-17-(propylthio)androsta-1,4-diene-3,16-dione.

* * * * *